US011098085B2

(12) United States Patent
Boden

(10) Patent No.: US 11,098,085 B2
(45) Date of Patent: Aug. 24, 2021

(54) USE OF A HIV DERIVED ACCESSORY PROTEIN FOR THE REACTIVATION OF LATENT HIV

(71) Applicant: Janssen Sciences Ireland Unlimited Company, County Cork (IE)

(72) Inventor: Daniel Boden, San Mateo, CA (US)

(73) Assignee: Janssen Sciences Ireland Unlimited Company, County Cork (IE)

( * ) Notice: Subject to any disclaimer, the term of this patent is extended or adjusted under 35 U.S.C. 154(b) by 0 days.

(21) Appl. No.: 16/460,872

(22) Filed: Jul. 2, 2019

(65) Prior Publication Data

US 2019/0337992 A1    Nov. 7, 2019

Related U.S. Application Data

(62) Division of application No. 15/306,218, filed as application No. PCT/EP2015/058747 on Apr. 23, 2015, now abandoned.

(30) Foreign Application Priority Data

Apr. 24, 2014  (EP) .................................... 14165811

(51) Int. Cl.
  *C07K 14/005*   (2006.01)
  *A61K 38/16*    (2006.01)
  *A61K 45/06*    (2006.01)

(52) U.S. Cl.
  CPC .......... *C07K 14/005* (2013.01); *A61K 38/162* (2013.01); *A61K 45/06* (2013.01); *C07K 2319/71* (2013.01); *C12N 2740/16033* (2013.01); *C12N 2740/16322* (2013.01)

(58) Field of Classification Search
  CPC ............ C12N 15/1034; C12N 15/1044; C12N 15/1062; C12N 15/1075; C12N 15/1079; C12N 2799/027; C12P 1/00
  See application file for complete search history.

(56) References Cited

U.S. PATENT DOCUMENTS

| 6,589,763 B1 | 7/2003 | Von Laer et al. | |
| 2002/0064798 A1* | 5/2002 | Nolan ................ | C12N 15/1062 435/7.1 |
| 2005/0221288 A1 | 10/2005 | Mathews et al. | |
| 2008/0124308 A1 | 5/2008 | Laer et al. | |
| 2010/0168004 A1* | 7/2010 | Williams ............... | A61K 31/19 514/3.8 |
| 2011/0159025 A1* | 6/2011 | Littman ................. | A61K 39/21 424/188.1 |

FOREIGN PATENT DOCUMENTS

| EP | 1279404 A1 | 1/2003 |
| WO | WO/2000/43037 A2 | 7/2000 |
| WO | W0/2002/085938 A1 | 10/2002 |
| WO | W0/2004/056391 | 7/2004 |
| WO | WO/2011/113618 A1 | 9/2011 |
| WO | WO/2011/146612 A2 | 11/2011 |
| WO | WO/2012/018856 A2 | 2/2012 |

OTHER PUBLICATIONS

Fawell et al., Tat-mediated delivery of heterologous proteins into cells, Proc. Natl. Acad. Sci. USA, vol. 91:664-668 (Jan. 1994) (Year: 1994).*
Wagner et al., Angew. Chem. Int. Ed. Engl., vol. 22:816-828 (1983) (Year: 1983).*
Serfling et al., NFAT transcription factors in control of peripheral T cell tolerance, Eur. J. Immunol., vol. 36:2837-2843 (2006) (Year: 2006).*
Oeckinghaus et al., The NF-κB Family of Transcription Factors and Its Regulation, Cold Spring Harb Perspect Biol., vol. 1(4): a000034 (Oct. 2009) (Year: 2009).*
Extended European Search Report for European Application No. EP14165811.2 dated Oct. 15, 2014.
International Search Report and Written Opinion for International Application No. PCT/EP2015/058747 dated Jul. 15, 2015.
AGV33422.1, Genbank AGV33422.1, tat protein, partial [Human immunodeficiency virus 1], www.ncbi.nlm.nih.gov, 1 page (submitted Aug. 2013), also available at https://www.ncbi.nlm.nih.gov/protein/AGV33422.1 (last visited Nov. 7, 2018) (Year: 2013).
AAP33732.1 (Genbank AAP33732.1, tat protein, partial [Human immunodeficiency virus 1], www.ncbi.nlm.nih.gov, 1 page (submitted 2002), also available at https://www.ncbi.nlm.nih.gov/protein/AAP33732.1 (last visited Nov. 7, 2018) (Year: 2002).

* cited by examiner

*Primary Examiner* — Randall L Beane

(57) ABSTRACT

The present invention concerns the use of a protein comprising at least a HIV-derived accessory protein tat (transactivator of transcription) or any derivative thereof for the reactivation of latent human immunodeficiency virus (HIV) from cells present in a HIV-infected patient.

14 Claims, No Drawings

Specification includes a Sequence Listing.

USE OF A HIV DERIVED ACCESSORY PROTEIN FOR THE REACTIVATION OF LATENT HIV

CROSS-REFERENCE TO RELATED APPLICATIONS

This application is a divisional of U.S. application Ser. No. 15/306,218, filed Oct. 24, 2016, pending, which is a national phase entry of International Application No. PCT/EP2015/058747, filed on Apr. 23, 2015, which claims priority to EP Patent Application No. 14165811.2, filed Apr. 24, 2014, each of which is incorporated herein in its entirety.

SEQUENCE LISTING

The instant application contains a Sequence Listing which has been submitted electronically in ASCII format and is hereby incorporated by reference in its entirety. Said ASCII copy, created on Oct. 20, 2016, and modified on Jul. 2, 2019 to update the bibliographic information, is named TIP0319USPCD1_SL.txt and is 6,526 bytes in size.

The present invention relates to the use of a protein comprising at least a HIV-derived accessory protein tat (trans-activator of transcription) or any derivative thereof for the reactivation of latent human immunodeficiency virus (HIV) from cells in an HIV-infected individual.

Highly active antiretroviral therapy (HAART) can suppress HIV-1 levels in plasma to below the limit of detection of clinical assays (<50 copies/ml) and reduce the morbidity and mortality of HIV-1 infection. However, HAART alone fails to cure HIV infection. In particular, HAART leaves latent integrated proviruses unaffected. Latent viral genomes reside in a small pool of infected resting memory CD4+ T-cells that constitute a stable viral reservoir. In these cells, the provirus remains transcriptionally silent as long as the host cells are in a quiescent state. This allows the virus to evade host immune surveillance and rebound quickly following discontinuation of HAART. The remarkable stability of the latent viral reservoir necessitates lifelong HAART. Given the potential for toxicity and resistance, elimination of the latent reservoir has been proposed as a goal worthy of a major scientific effort.

Therapies targeting the latent reservoir generally involve reactivation of latent virus. Expression of viral genes renders infected cells susceptible to viral cytopathic effects and immune clearance. Along with HAART, this reactivation strategy could ultimately purge latent virus from infected individuals. While latent viruses respond to T-cell activation signals initial attempts to deplete the latent reservoir through T-cell reception (TCR) stimulation using anti-CD3 antibodies proved toxic. The toxicity likely resulted from global T-cell activation with subsequent release of pro-inflammatory cytokines. Therefore, an ideal treatment should reactivate latent HIV-1, but avoid overall T-cell activation.

However, despite global extensive research efforts, there still exists a high unmet medical need for reliable, safe and convenient compounds able to reactivate latent HIV from above mentioned reservoir in HIV-infected patients.

The current invention aims to using a mutant of the HIV-derived accessory protein tat (trans-activator of transcription) for the reactivation and subsequent eradication of latent HIV. The full length tat protein [86-101 aa] is translated from two different exons where exon-1 [1-72 aa] contains all domains essential for trans-activation. Mutagenesis experiments surprisingly identified the first 57 N-terminal amino acids of wild type tat as minimal reactivation domain (Table 2). The 66 amino acid deletion mutant [T66] with a reactivation capacity close to full length exon 1 Tat72 (Table 2) potently activates HIV in latently infected cell lines (Table 3) and primary CD4 cells (Table 4). The activity of Tat derivatives was evaluated ex vivo on patient-derived latently infected CD4 cells and compared with the most potent reference compounds known to reactivate latent HIV in vitro and ex vivo. Unexpectedly Tat 66 protein induced HIV activation and exceeded by far the reactivation achieved by reference compounds such as PHA (Phytohaemagglutinin), PMA (Phorbol myristate acetate), and SAHA (suberoyl anilide hydroxamic acid). The inclusion of a tat-derived protein in a treatment regimen will be essential to cure HIV infected people.

The current invention thus relates to the use of a protein comprising at least a HIV-derived accessory protein tat (trans-activator of transcription) or any derivative thereof for the reactivation of latent human immunodeficiency virus (HIV) from cells present in a HIV-infected patient.

Alternatively it can be expressed that the invention concerns a method of reactivating latent HIV present in a host cell by exposing a HIV infected cell with a HIV-derived accessory protein tat (trans-activator of transcription) or any derivative thereof.

Tat stands for, as mentioned above, "Trans-Activator of Transcription" and Tat consists of between 86 and 101 amino acids depending on the subtype.

Also, in molecular biology, tat is a protein which is encoded for by the tat gene in HIV-1. Tat is a regulatory protein that drastically enhances the efficiency of viral transcription.

Preferably said protein comprises at least a wild-type HIV-derived accessory protein tat for the reactivation of latent HIV but more preferably said protein comprises at least the first 57 N-terminal amino acids of wild-type tat (86-101 aa) for the reactivation of latent HIV.

Said protein may also comprise at least the first 60 N-terminal amino acids of wild-type tat (86-101 aa) for the reactivation of latent HIV.

Said 57 amino acids are represented by the following SEQ ID No. 1:

MEPVDPRLEPWKHPGSQPKTACTNCYCKKCCFHCQVCFMTKALGISYGRK
KRRQRRR.

The mentioned 60 amino acids are represented by the following SEQ ID No; 2:

MEPVDPRLEPWKHPGSQPKTACTNCYCKKCCFHCQVCFMTKALGISYGRK
KRRQRRRAHQ

The 66 amino acid deletion mutant [T66] according to the invention with a reactivation capacity close to full length exon 1 Tat72 has the amino acid sequence of SEQ ID NO 3:

MEPVDPRLEPWKHPGSQPKTACTNCYCKKCCFHCQVCFMTKALGISYGRK
KRRQRRRAHQNSQTHQ.

In Table 1 below substitutions are provided for each position in these SEQ ID NO: 1, 2 and 3 respectively which are feasible in order to obtain a protein falling within the scope of the present invention.

TABLE 1

| Primary T66 amino acid sequence with indicated substitutions | | |
|---|---|---|
| No | T66 | Substitutions |
| 1. | M | |
| 2. | E | D |
| 3. | P | L |
| 4. | V | I |
| 5. | D | N |
| 6. | P | H |
| 7. | R | N/S/K |
| 8. | L | I |
| 9. | E | D |
| 10. | P | |
| 11. | W | |
| 12. | K | N/E/Q/H |
| 13. | H | Q/R |
| 14. | P | S |
| 15. | G | |
| 16. | S | |
| 17. | Q | R/K |
| 18. | P | |
| 19. | K | R/T/A/I/S/Q/N/E/G/P |
| 20. | T | |
| 21. | A | P/D/N/E/S |
| 22. | C | |
| 23. | T | N/S |
| 24. | N | K/P/T/S/A/Q/R/G |
| 25. | C | |
| 26. | Y | F |
| 27. | C | |
| 28. | K | |
| 29. | K | R/H/A/M/V/Q/E/S/I/Y |
| 30. | C | |
| 31. | C | S |
| 32. | F | Y/W/L/M |
| 33. | H | |
| 34. | C | |
| 35. | Q | L/P/Y/I/V/M/A/T |
| 36. | V | L/W/A/I/S/Y/M/D/K/H/N/R/T/F/C |
| 37. | C | |
| 38. | F | L |

TABLE 1-continued

| Primary T66 amino acid sequence with indicated substitutions | | |
|---|---|---|
| No | T66 | Substitutions |
| 39. | M | T/Q/I/L/H/V/A/S |
| 40. | T | K/N/H/Q/S/R/A/T/D |
| 41. | K | |
| 42. | A | G |
| 43. | L | |
| 44. | G | S/R |
| 45. | I | T/V/L |
| 46. | S | F/Y/V/I/C/P/L/H/R |
| 47. | Y | H/N |
| 48. | G | |
| 49. | R | K |
| 50. | K | R |
| 51. | K | R |
| 52. | R | W/Q |
| 53. | R | K/S/G/T/Q/N |
| 54. | Q | H/R/P/L/K/S |
| 55. | R | Q/H |
| 56. | R | H/P/Q/T/S |
| 57. | R | G/S/T/N/K/A/P/Q |
| 58. | A | T/P/S |
| 59. | H | P/S/A/T |
| 60. | Q | P/H/R/E/K/N/Y/L |
| 61. | N | S/D/G/R/C/A/H |
| 62. | S | N/G/Y/R/D/C/H |
| 63. | Q | K/E/G/P/S/T/A/R |
| 64. | T | D/A/I/N/S/P/G/V/H/E/L |
| 65. | H | N/D/Y/R |
| 66. | Q | K |

(SEQ ID NO: 4)

Definitions

By the term “amino acid” is meant, for purposes of the specification and claims and in reference to the protein according to the present invention, to refer to a molecule that has at least one free amine group and at least one free carboxyl group and may further comprise one or more free chemical reactive group other than an amine or a carboxyl group (e.g., a hydroxyl, a sulfhydryl, etc). The amino acid may be a naturally occurring amino acid (e.g., L-amino acid and is depicted in this specification as a capital letter in the sequence), a non-naturally occurring amino acid (e.g., D-amino acid and is depicted in this specification as a small letter in the sequence), a synthetic amino acid, a modified amino acid, an amino acid derivative, an amino acid precursor, and a conservative substitution.

A person skilled in the art would know that the choice of amino acids incorporated into a protein will depend, in part, on the specific physical, chemical or biological characteristics required of the protein. Such characteristics are determined, in part, by determination of helicity and activity. For example, a skilled person would know that amino acids in a synthetic protein may be comprised of one or more of naturally occurring (L-) amino acid and non-naturally occurring (D-) amino acid.

A "conservative substitution" is used in this specification to mean one or more amino acids substitution in the sequence of the protein such that the protein still demonstrate the unexpected, improved biological activity. This includes substitutions of amino acids having substantially the same charge, size, hydrophilicity, and/or aromaticity as the amino acid replaced.

Nomenclature Used in this Specification

For the L-natural amino acids, as known in the art, the following abbreviations were used:

|  | Symbol | |
| --- | --- | --- |
| Name | 3-Letter | 1-Letter |
| Alanine | Ala | A |
| Arginine | Arg | R |
| Asparagine | Asn | N |
| Aspartic acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Furthermore part of the invention is the use of any of the above mentioned proteins wherein said protein comprises in addition another protein forming a fusion protein. Examples of such domains fused to HIV tat are transactivation domains (TAD) of host transcription factors such as NFkB or NFAT. By using the specific recruitment of Tat to the HIV LTR, additional transactivation domains are delivered in close proximity to the HIV promoter and surprisingly result in additional activation. Table 5 shows the increased activity of T66 linked to TADs from NFkB p65 and NFAT2. Another option would be to add a cell-targeting moiety to HIV tat such as anti-CD3 antibody or IL7 to target the transactivator more specifically to cells that are known to harbor latent HIV.

The T66 protein is used in a concentration of 1 µM to 10 µM, preferably of 2 µM to 5 µM.

After the use of the protein according to the invention HIV can be eradicated by addition of an antiviral agent such as a small molecule and/or antibody directed towards HIV in order to realize a cure of HIV.

Part of the invention is also a pharmaceutical composition comprising the protein above referenced and a pharmaceutically accepted carrier.

To the present invention also belongs a method for treating a subject with human immunodeficiency virus (HIV) comprising the steps of:
  a) administering to said subject an effective amount of the pharmaceutical composition comprising the protein according to the invention and a pharmaceutically accepted carrier; and
  b) administering to said subject an effective amount of one or more anti-viral agent.

Experimental Part

TABLE 2

HIV LTR transactivation by Tat C-terminal deletion mutants.

| Tat variant | % Tat72 activity |
| --- | --- |
| 1-66 | 92.2 (±12.7) |
| 1-64 | 77.2 (±10.8) |
| 1-60 | 77.2 (±10.8) |
| 1-57 | 40.2 (±2.3) |
| 1-50 | 0.0 (NA) |

Activity is expressed in % with respect to the activity achieved by full length Tat72 exon-1 set to 100%. Shown data are mean values [n 4] with indicated (standard deviation).

Tat-mediated transactivation was determined by triple plasmid transfection of HEK293 cells with pEF-T, a Tat expression plasmid, LTR-FLuc, a HIV LTR-controlled firefly luciferase reporter plasmid and pEF1-RLuc, a EF1α promoter driven *Renilla* luciferase reporter plasmid. Luciferase reporter activities were assessed 24 h post transfection using the Dual-Glo luciferase assay [Promega]. The measured HIV LTR luciferase data were normalized by *Renilla* luciferase data retrieved from the pEF1-RLuc plasmid. LTR activity is expressed as percentage of wild type exon-1 Tat72 activity.

TABLE 3

Titration of tat protein variants on latent HIV LTR-GFP reporter cell line.

| Tat [µg] | 100 | 80 | 70 | 60 | 50 | 40 | 30 | 0 |
| --- | --- | --- | --- | --- | --- | --- | --- | --- |
| T72 | 93.7 | 93.8 | 88.8 | 76.3 | 60.4 | 47.2 | 18.6 | 1.2 |
| T66 | 94.5 | 93.9 | 87.6 | 88.7 | 87.0 | 53.8 | 45.7 | 1.0 |
| T60 | 93.3 | 95.8 | 95.2 | 92.1 | 87.0 | 33.4 | 28.5 | 1.1 |

MT4-LTR-GFP cells were incubated overnight with different Tat variants at the indicated concentration [µg/ml]. LTR activation was determined by flow cytometry.

TABLE 4

Ex vivo activation of CD4 cells with Tat protein T60, T66, and T86.

| | % Activity (PMA/PHA) | | | | |
| --- | --- | --- | --- | --- | --- |
| Tat | Donor 1 | Donor 2 | Donor 3 | Donor 4 | Donor 5 |
| T60 | 405/328 | ND | 213/196 | ND | ND/254 |
| T66 | 838/680 | 1121/986 | 530/487 | ND/479 | ND/636 |
| T86 | ND | ND | ND | ND/436 | ND/408 |

Activation of latent HIV from primary CD4+ T cells by overnight incubation with different Tat proteins. Indicated numbers represent HIV activation in percentage to reference compounds PMA and PHA set to 100%. The shown % increase compared to PMA/PHA is statistically significant ($p<0.01$).

CD4+ T cells were isolated from 200 ml whole blood using CD4 microbeads (Miltenyi Biotec) according to manufacturer's protocol. Blood originates from HIV-infected individuals under long-term HAART with undetectable plasma virus. Ten to twenty replicates of cell pools plated at $1\times10^6$ CD4+ T cells/well were incubated overnight with compounds or mock controls (DMSO/PBS). Total RNA was isolated from each replicate using the Magmax 96 Total RNA isolation kit (Ambion) following the manufacturer's protocol. Duplicate cDNA reactions were performed on each RNA replicate using SuperScript III First-Strand Synthesis kit (Invitrogen) according to the manufacturer's protocol. Quantitative real-time PCR (QPCR) was conducted on each cDNA applying gag-specific primers and the nucleic acid detection dye Sybr Green I [Invitrogen]. Standard curves were generated using cDNA synthesized from in vitro transcribed RNA. The detection limit of the QPCR assay was determined to be within 1-10 copies/reaction. Cycle threshold (ct) values 40 were excluded from the analysis. The Wilcoxon rank sum test was used to calculate the statistical significance of the relative HIV-1 gag RNA copy number between different conditions.

TABLE 5

T66 fusion proteins result in increased activation when compared to T66.

| pEF-T ID | FLUC | RLUC | $FLUC_{norm}$ | Fold | % T66 |
|---|---|---|---|---|---|
| T66 | 15437 | 267 | 37049 | 26 | 100 |
| T66-NFK114 | 25480 | 380 | 42918 | 30 | 116 |
| T66-NFAT2C | 22614 | 304 | 47674 | 33 | 129 |
| Cell control | 1450 | 641 | 1448 | 1 | 4 |

Triple plasmid transfection of HEK293 cells with pEF-T (Tat expression plasmid), LTR-FLuc (HIV LTR-controlled firefly luciferase reporter plasmid) and pEF1-RLuc (EF1α promoter driven *Renilla* luciferase reporter plasmid). Luciferase reporter activities were assessed 24 h post transfection using the Dual-Glo luciferase assay [Promega]. The measured HIV LTR luciferase data were normalized by *Renilla* luciferase data collected from the co-transfected pEF1-RLuc signal. LTR activation is either expressed as fold increase over cell control or as percentage of T66 activity.

The invention claimed is:

1. A method of reversing HIV-1 latency in an HIV infected cell, comprising exposing the HIV infected cell to a mutant protein of an HIV Tat which consists of the amino acid sequence selected from the group consisting of SEQ ID NO:1, SEQ ID NO:2 and SEQ ID NO:3.

2. A method of reversing HIV-1 latency in an HIV infected cell, comprising exposing the HIV infected cell to a fusion protein which consists of mutant protein fused to a transactivation domain, wherein the mutant protein consists of either SEQ ID NO:1, SEQ ID NO:2 or SEQ ID NO:3; and wherein the transactivation domain consists of the transactivation domain of either NFκB p65 or NFAT2.

3. The method of claim 1, wherein said amino acid sequence is SEQ ID NO:1.

4. The method of claim 1, wherein said amino acid sequence is SEQ ID NO:2.

5. The method of claim 1, wherein said amino acid sequence is SEQ ID NO:3.

6. The method of claim 2, wherein said mutant protein consists of SEQ ID NO:1.

7. The method of claim 6, wherein said transactivation domain is the transactivation domain of NFκB p65.

8. The method of claim 6, wherein said transactivation domain is the transactivation domain of NFAT2.

9. The method of claim 2, wherein said mutant protein consists of SEQ ID NO:2.

10. The method of claim 9, wherein said transactivation domain is the transactivation domain of NFκB p65.

11. The method of claim 9, wherein said transactivation domain is the transactivation domain of NFAT2.

12. The method of claim 2, wherein said mutant protein consists of SEQ ID NO:3.

13. The method of claim 12, wherein said transactivation domain is the transactivation domain of NFκB p65.

14. The method of claim 12, wherein said transactivation domain is the transactivation domain of NFAT2.

* * * * *

SEQUENCE LISTING

<160> NUMBER OF SEQ ID NOS: 4

<210> SEQ ID NO 1
<211> LENGTH: 57
<212> TYPE: PRT
<213> ORGANISM: Human immunodeficiency virus 1

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg
    50                  55

<210> SEQ ID NO 2
<211> LENGTH: 60
<212> TYPE: PRT
<213> ORGANISM: Human immunodeficiency virus 1

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Arg Ala His Gln
    50                  55                  60

<210> SEQ ID NO 3
<211> LENGTH: 66
<212> TYPE: PRT
<213> ORGANISM: Human immunodeficiency virus 1

<400> SEQUENCE: 3

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln
65

<210> SEQ ID NO 4
<211> LENGTH: 66
<212> TYPE: PRT
<213> ORGANISM: Human immunodeficiency virus 1
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Pro or Leu
<220> FEATURE:
<221> NAME/KEY: MOD_RES
<222> LOCATION: (4)..(4)
<223> OTHER INFORMATION: Val or Ile
<220> FEATURE:
<221> NAME/KEY: MOD_RES
<222> LOCATION: (5)..(5)
<223> OTHER INFORMATION: Asp or Asn
<220> FEATURE:
<221> NAME/KEY: MOD_RES
<222> LOCATION: (6)..(6)
<223> OTHER INFORMATION: Pro or His
<220> FEATURE:
<221> NAME/KEY: MOD_RES
<222> LOCATION: (7)..(7)
<223> OTHER INFORMATION: Arg, Asn, Ser or Lys
<220> FEATURE:
<221> NAME/KEY: MOD_RES
<222> LOCATION: (8)..(8)
<223> OTHER INFORMATION: Leu or Ile
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (12)..(12)
<223> OTHER INFORMATION: Lys, Asn, Glu, Gln or His
<220> FEATURE:
<221> NAME/KEY: MOD_RES
<222> LOCATION: (13)..(13)
<223> OTHER INFORMATION: His, Gln or Arg
<220> FEATURE:
<221> NAME/KEY: MOD_RES
<222> LOCATION: (14)..(14)
<223> OTHER INFORMATION: Pro or Ser
<220> FEATURE:
<221> NAME/KEY: MOD_RES
<222> LOCATION: (17)..(17)
<223> OTHER INFORMATION: Gln, Arg or Lys
<220> FEATURE:
<221> NAME/KEY: MOD_RES
<222> LOCATION: (19)..(19)
<223> OTHER INFORMATION: Lys, Arg, Thr, Ala, Ile, Ser, Gln, Asn, Glu,
    Gly or Pro
<220> FEATURE:
<221> NAME/KEY: MOD_RES
<222> LOCATION: (21)..(21)

-continued

```
<223> OTHER INFORMATION: Ala, Pro, Asp, Asn, Glu or Ser
<220> FEATURE:
<221> NAME/KEY: MOD_RES
<222> LOCATION: (23)..(23)
<223> OTHER INFORMATION: Thr, Asn or Ser
<220> FEATURE:
<221> NAME/KEY: MOD_RES
<222> LOCATION: (24)..(24)
<223> OTHER INFORMATION: Asn, Lys, Pro, Thr, Ser, Ala, Gln, Arg or Gly
<220> FEATURE:
<221> NAME/KEY: MOD_RES
<222> LOCATION: (26)..(26)
<223> OTHER INFORMATION: Tyr or Phe
<220> FEATURE:
<221> NAME/KEY: MOD_RES
<222> LOCATION: (29)..(29)
<223> OTHER INFORMATION: Lys, Arg, His, Ala, Met, Val, Gln, Glu, Ser,
      Ile or Tyr
<220> FEATURE:
<221> NAME/KEY: MOD_RES
<222> LOCATION: (31)..(31)
<223> OTHER INFORMATION: Cys or Ser
<220> FEATURE:
<221> NAME/KEY: MOD_RES
<222> LOCATION: (32)..(32)
<223> OTHER INFORMATION: Phe, Tyr, Trp, Leu or Met
<220> FEATURE:
<221> NAME/KEY: MOD_RES
<222> LOCATION: (35)..(35)
<223> OTHER INFORMATION: Gln, Leu, Pro, Tyr, Ile, Val, Met, Ala or Thr
<220> FEATURE:
<221> NAME/KEY: MOD_RES
<222> LOCATION: (36)..(36)
<223> OTHER INFORMATION: Val, Leu, Trp, Ala, Ile, Ser, Tyr, Met, Asp,
      Lys, His, Asn, Arg, Thr, Phe or Cys
<220> FEATURE:
<221> NAME/KEY: MOD_RES
<222> LOCATION: (38)..(38)
<223> OTHER INFORMATION: Phe or Leu
<220> FEATURE:
<221> NAME/KEY: MOD_RES
<222> LOCATION: (39)..(39)
<223> OTHER INFORMATION: Met, Thr, Gln, Ile, Leu, His, Val, Ala or Ser
<220> FEATURE:
<221> NAME/KEY: MOD_RES
<222> LOCATION: (40)..(40)
<223> OTHER INFORMATION: Thr, Lys, Asn, His, Gln, Ser, Arg, Ala, Thr or
      Asp
<220> FEATURE:
<221> NAME/KEY: MOD_RES
<222> LOCATION: (42)..(42)
<223> OTHER INFORMATION: Ala or Gly
<220> FEATURE:
<221> NAME/KEY: MOD_RES
<222> LOCATION: (44)..(44)
<223> OTHER INFORMATION: Gly, Ser or Arg
<220> FEATURE:
<221> NAME/KEY: MOD_RES
<222> LOCATION: (45)..(45)
<223> OTHER INFORMATION: Ile, Thr, Val or Leu
<220> FEATURE:
<221> NAME/KEY: MOD_RES
<222> LOCATION: (46)..(46)
<223> OTHER INFORMATION: Ser, Phe, Tyr, Val, Ile, Cys, Pro, Leu, His or
      Arg
<220> FEATURE:
<221> NAME/KEY: MOD_RES
<222> LOCATION: (47)..(47)
<223> OTHER INFORMATION: Tyr, His or Asn
<220> FEATURE:
<221> NAME/KEY: MOD_RES
<222> LOCATION: (49)..(49)
<223> OTHER INFORMATION: Arg or Lys
<220> FEATURE:
<221> NAME/KEY: MOD_RES
<222> LOCATION: (50)..(50)
<223> OTHER INFORMATION: Lys or Arg
<220> FEATURE:
<221> NAME/KEY: MOD_RES
```

```
<222> LOCATION: (51)..(51)
<223> OTHER INFORMATION: Lys or Arg
<220> FEATURE:
<221> NAME/KEY: MOD_RES
<222> LOCATION: (52)..(52)
<223> OTHER INFORMATION: Arg, Trp or Gln
<220> FEATURE:
<221> NAME/KEY: MOD_RES
<222> LOCATION: (53)..(53)
<223> OTHER INFORMATION: Arg, Lys, Ser, Gly, Thr, Gln or Asn
<220> FEATURE:
<221> NAME/KEY: MOD_RES
<222> LOCATION: (54)..(54)
<223> OTHER INFORMATION: Gln, His, Arg, Pro, Leu, Lys or Ser
<220> FEATURE:
<221> NAME/KEY: MOD_RES
<222> LOCATION: (55)..(55)
<223> OTHER INFORMATION: Arg, Gln or His
<220> FEATURE:
<221> NAME/KEY: MOD_RES
<222> LOCATION: (56)..(56)
<223> OTHER INFORMATION: Arg, His, Pro, Gln, Thr or Ser
<220> FEATURE:
<221> NAME/KEY: MOD_RES
<222> LOCATION: (57)..(57)
<223> OTHER INFORMATION: Arg, Gly, Ser, Thr, Asn, Lys, Ala, Pro or Gln
<220> FEATURE:
<221> NAME/KEY: MOD_RES
<222> LOCATION: (58)..(58)
<223> OTHER INFORMATION: Ala, Thr, Pro or Ser
<220> FEATURE:
<221> NAME/KEY: MOD_RES
<222> LOCATION: (59)..(59)
<223> OTHER INFORMATION: His, Pro, Ser, Ala or Thr
<220> FEATURE:
<221> NAME/KEY: MOD_RES
<222> LOCATION: (60)..(60)
<223> OTHER INFORMATION: Gln, Pro, His, Arg, Glu, Lys, Asn, Tyr or Leu
<220> FEATURE:
<221> NAME/KEY: MOD_RES
<222> LOCATION: (61)..(61)
<223> OTHER INFORMATION: Asn, Ser, Asp, Gly, Arg, Cys, Ala or His
<220> FEATURE:
<221> NAME/KEY: MOD_RES
<222> LOCATION: (62)..(62)
<223> OTHER INFORMATION: Ser, Asn, Gly, Tyr, Arg, Asp, Cys or His
<220> FEATURE:
<221> NAME/KEY: MOD_RES
<222> LOCATION: (63)..(63)
<223> OTHER INFORMATION: Gln, Lys, Glu, Gly, Pro, Ser, Thr, Ala or Arg
<220> FEATURE:
<221> NAME/KEY: MOD_RES
<222> LOCATION: (64)..(64)
<223> OTHER INFORMATION: Thr, Asp, Ala, Ile, Asn, Ser, Pro, Gly, Val,
      His, Glu or Leu
<220> FEATURE:
<221> NAME/KEY: MOD_RES
<222> LOCATION: (65)..(65)
<223> OTHER INFORMATION: His, Asn, Asp, Tyr or Arg
<220> FEATURE:
<221> NAME/KEY: MOD_RES
<222> LOCATION: (66)..(66)
<223> OTHER INFORMATION: Gln or Lys

<400> SEQUENCE: 4

Met Xaa Xaa Xaa Xaa Xaa Xaa Xaa Xaa Pro Trp Xaa Xaa Xaa Gly Ser
1               5                   10                  15

Xaa Pro Xaa Thr Xaa Cys Xaa Xaa Cys Xaa Cys Lys Xaa Cys Xaa Xaa
            20                  25                  30

His Cys Xaa Xaa Cys Xaa Xaa Xaa Lys Xaa Leu Xaa Xaa Xaa Xaa Gly
        35                  40                  45
```

-continued

```
Xaa Xaa Xaa Xaa Xaa Xaa Xaa Xaa Xaa Xaa Xaa Xaa Xaa Xaa Xaa
    50                  55                  60

Xaa Xaa
65
```